(12) United States Patent
Kim (10) Patent No.: US 11,009,506 B2
(45) Date of Patent: May 18, 2021

(54) KIT FOR RAPID DIAGNOSIS OF ASTHMA OR ALLERGY DISEASE

(71) Applicant: INJE UNIVERSITY INDUSTRY-ACADEMIC COOPERATION FOUNDATION, Gimhae-si (KR)

(72) Inventor: Chang-Keun Kim, Seoul (KR)

(73) Assignee: INJE UNIVERSITY INDUSTRY-ACADEMIC COOPERATION FOUNDATION, Gimhae-si (KR)

( * ) Notice: Subject to any disclaimer, the term of this patent is extended or adjusted under 35 U.S.C. 154(b) by 54 days.

(21) Appl. No.: 16/485,024

(22) PCT Filed: Feb. 9, 2018

(86) PCT No.: PCT/KR2018/001757
§ 371 (c)(1),
(2) Date: Aug. 9, 2019

(87) PCT Pub. No.: WO2018/147679
PCT Pub. Date: Aug. 16, 2018

(65) Prior Publication Data
US 2020/0041506 A1 Feb. 6, 2020

(30) Foreign Application Priority Data
Feb. 10, 2017 (KR) .................. 10-2017-0018517

(51) Int. Cl.
*G01N 33/558* (2006.01)
*G01N 33/564* (2006.01)
(Continued)

(52) U.S. Cl.
CPC .......... *G01N 33/564* (2013.01); *G01N 33/553* (2013.01); *G01N 33/558* (2013.01); *G01N 33/577* (2013.01)

(58) Field of Classification Search
CPC .. G01N 33/564; G01N 33/553; G01N 33/558; G01N 33/577; G01N 2800/122;
(Continued)

(56) References Cited

FOREIGN PATENT DOCUMENTS

| KR | 10-2015-0145986 A | 12/2015 |
|---|---|---|
| KR | 10-1611743 B1 | 4/2016 |

OTHER PUBLICATIONS

Morioka et al, "Development of a novel enzyme-linked immunosorbent assay for blood and urinary eosinophil derived neurotoxin: A preliminary study in patients with bronchial asthma", International Archives of Allergy and Immunology, May 2000, 122, 1, 49-47. (Year: 2000).*

(Continued)

*Primary Examiner* — Christopher L Chin
(74) *Attorney, Agent, or Firm* — Sughrue Mion, PLLC (57) ABSTRACT

Provided is a kit for asthma diagnosis comprising a strip including a base part, a first reaction part formed on the base part, and a developing membrane formed between the first reaction part and the base part, in which the first reaction part includes a monoclonal antibody expressed from a hybridoma cell line of Accession Number KCLRF-BP-00389 (Accession Date: Jan. 9, 2017, Accession Institute: Korea Cell Line Research Foundation (KCLRF)) and the second reaction part includes a monoclonal antibody expressed from a hybridoma cell line of Accession Number KCLRF-BP-00389 (Accession Date: Jan. 9, 2017, Accession Institute: Korea Cell Line Research Foundation (KCLRF)).

8 Claims, 5 Drawing Sheets

(51) Int. Cl.
*G01N 33/553* (2006.01)
*G01N 33/577* (2006.01)

(58) Field of Classification Search
CPC .. G01N 33/581; G01N 33/585; G01N 33/582; B01L 2300/0825
USPC ..... 422/400, 401, 420, 425, 430; 435/287.7, 435/287.9, 970, 805, 810; 436/169, 518, 436/514, 530, 810, 805, 811
See application file for complete search history.

(56) References Cited

OTHER PUBLICATIONS

Chang-Keun Kim, MD, "Eosinophil-derived neurotoxin: a novel biomarker for diagnosis and monitoring of asthma", Korean Journal of Pediatrics, 2013, pp. 8-12, vol. 56, No. 1.
Chang-Keun Kim et al., "Utility of serum eosinophil-derived neurotoxin (EDN) measurement by ELISA in young children with asthma", Allergology International, 2017, pp. 70-74, vol. 66.
Junichiro Morioka et al., "Development of a Novel Enzyme-Linked immunosorbent Assay for Blood and Urinary Eosinophil-Derived Neurotoxin: A Preliminary Study in Patients with Bronchial Asthma", International Archives of Allergy and Immunology, 2000, pp. 49-57, vol. 122, No. 49.
International Search Report for PCT/KR2018/001757 dated, Jun. 19, 2018 (PCT/ISA/210).

\* cited by examiner

KIT FOR RAPID DIAGNOSIS OF ASTHMA OR ALLERGY DISEASE

CROSS REFERENCE TO RELATED APPLICATIONS

This application is a National Stage of International Application No. PCT/KR2018/001757 filed Feb. 9, 2018, claiming priority based on Korean Patent Application No. 10-2017-0018517, filed Feb. 10, 2017, the entire disclosures of which are incorporated herein by reference.

TECHNICAL FIELD

The present invention relates to a kit for diagnosis of asthma or allergy disease. The present invention relates to a kit capable of rapidly diagnosing asthma or allergy disease, which has not been easily diagnosed in infants or children in the related art, within 20 minutes using an immunochromatographic method at the outside (hospital and outpatient) or at home.

BACKGROUND ART

Asthma and allergy diseases are increasing worldwide in prevalence and severity. In the United States, 7% of children have suffered from asthma, and 15% of children also suffered from chronic rhinosinusitis, an airway disease similar to bronchial asthma. Diagnosis of these diseases is not easy, and thus until recently, there is no simple diagnostic method to help diagnosis of doctors or prevent the disease from deteriorating. Although it is generally known that chronic airway inflammation reaction is occurring in the airways of patients with asthma or allergy disease, there is no simple clinical diagnosis except for several experimental immunoassays for the purpose of researches for measuring airway inflammation reaction.

In particular, it is difficult to distinguish whether airway inflammation is caused by an infection of a microorganism such as a bacterial infection or by an allergic immune response in an allergy disease such as asthma. For this reason, patients with asthma or allergy disease often receive the wrong treatment, such as receiving antibiotics for a long period of time.

Currently, a pulmonary function test and a methacholine bronchial challenge test, which are used for the diagnosis of bronchial asthma, have difficulties in various applications. In order to obtain accurate results, well-managed equipment, skilled testers, and positive responses of patients are required. For this reason, it is a fact that it is difficult to perform the tests in infants under 6 years old or children, elderly people, physically handicapped people, patients currently suffering from severe asthma, etc., who have difficult responses of the patients.

In addition, since it is necessary to consume a large amount of physical strength, it is often difficult for the patient to repeatedly perform the test because the patient is likely to have a sense of resistance to the test. Therefore, there has been an attempt to develop a noninvasive or hematological test that has been helpful in the diagnosis of asthma in the past, which corresponds to a method for an eosinophil count in the blood, serum eosinophil cationic proteins (ECP), etc. which have been adjunctively used in asthmatic patients currently. These methods are known to have a large individual difference in normal people, other allergy diseases, asthma, and the like, not to be used for diagnosis.

Therefore, if a simple diagnostic tool can be developed to measure the eosinophilic inflammatory response, which is the most important immune response in asthma and allergy diseases, it is possible to innovatively contribute to the diagnosis and treatment of diseases such as asthma.

DISCLOSURE

Technical Problem

An object of the present invention is to provide a kit capable of rapidly diagnosing asthma or allergy disease with high reliability.

Technical Solution

A kit for asthma diagnosis of the present invention may comprise a strip including a base part; a first reaction part formed on the base part and including a monoclonal antibody expressed from a hybridoma cell line (Accession Number KCLRF-BP-00389); and a developing membrane formed between the first reaction part and the base part and including a second reaction part including a monoclonal antibody expressed from a hybridoma cell line (Accession Number KCLRF-BP-00389).

A kit for allergy diagnosis of the present invention may comprise a strip including a base part; a first reaction part formed on the base part and including a monoclonal antibody expressed from a hybridoma cell line (Accession Number KCLRF-BP-00389); and a developing membrane formed between the first reaction part and the base part and including a second reaction part including a monoclonal antibody expressed from a hybridoma cell line (Accession Number KCLRF-BP-00389).

Advantageous Effects

The present invention provides a kit for rapidly diagnosing asthma or allergy disease with high reliability and predicting and monitoring a prognosis in asthma or allergy disease.

DESCRIPTION OF DRAWINGS

FIG. 2A illustrates a result of the EDN, FIG. 2B illustrates a result of the ECP, and FIG. 2C illustrates results of the total eosinophil count and the asthma symptom scores.

MODES OF THE INVENTION

Exemplary embodiments of the present invention will be described more fully hereinafter with reference to the accompanying drawings so as to be easily implemented by those skilled in the art. The present invention may be implemented in various different forms and is not limited to exemplary embodiments described herein. Parts not associated with required description are omitted for clearly describing the present invention and like reference numerals designate like elements throughout the specification.

In this specification, the terms "upper" and "lower" are defined with reference to the drawings, wherein "upper" may be changed to "lower" and "lower" may be changed to "upper" according to a view point, and the term "on" may include not only directly on but also intervening another structure. Meanwhile, "directly on" means not intervening another structure.

Figure 1:
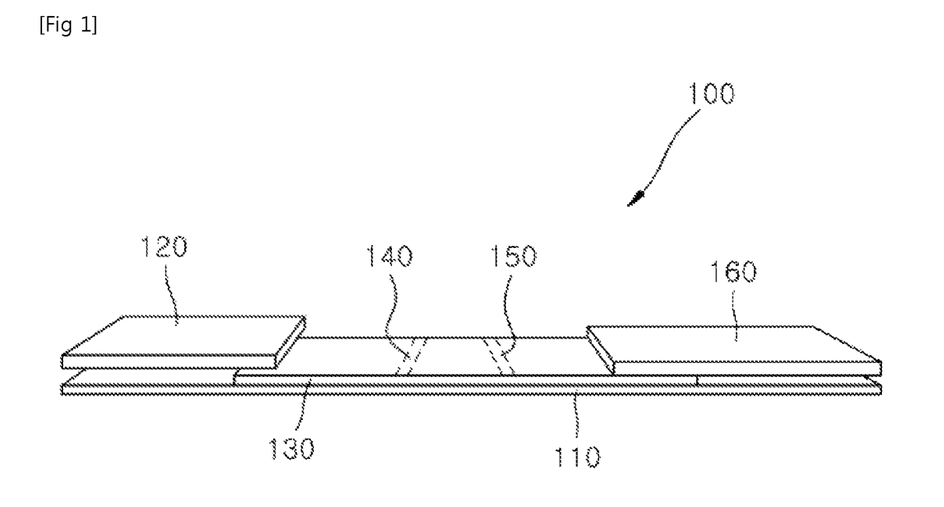
FIG. 1 is a schematic diagram of a strip included in a kit for asthma diagnosis according to an exemplary embodiment of the present invention.

In this specification, the term "hybridoma" refers to a cell made by artificially fusing two different types of cells. The hybridoma cell is produced by fusing two or more homologous cells or xenogeneic cells using a substance that causes cell fusion such as polyethylene glycol or a specific species of virus and different functions of different cells may be integrated into one cell by forming the hybridoma cell. For the purposes of the present invention, a monoclonal antibody produced from a hybridoma cell line of Accession Number KCLRF-BP-00389 (Accession Date: Jan. 9, 2017, Accession Institute: Korea Cell Line Research Foundation (KCLRF)) may be used. Eosinophil-derived neurotoxin (EDN) contained in a sample is bound to the monoclonal antibody in a first reaction part 120 and then reaches a second reaction part 140 while moving through a developing membrane 130 to be detected by binding with the monoclonal antibody in the second reaction part 140.

The term "monoclonal antibody" used in the present invention refers to a highly specific antibody directed against a single antigenic site (epitope) as known in the art. Unlike polyclonal antibodies, which typically contain different antibodies directed against different epitopes, the monoclonal antibody is directed against a single epitope on the antigen. The monoclonal antibody has an advantage of improving the selectivity and specificity of diagnostic and analytical assays using antigen-antibody binding and has an advantage of not being contaminated by other immunoglobulins because the monoclonal antibody may be produced by the culture or a phage display method of a fusion cell line (hybridoma).

The monoclonal antibody of the present invention may be used in an unpurified state, but may be purified and used as needed according to a method commonly used in the art. Examples of such a purification method include dialysis, salt precipitation, ion exchange chromatography, size exclusion chromatography, affinity chromatography and the like, but the method of purifying the antibody of the present invention is not limited by the examples.

The monoclonal antibody of the present invention also includes a functional fragment of an antibody molecule as well as a form having a heavy-chain variable region and a light-chain variable region as long as the monoclonal antibody recognizes a specific epitope of the antigen and has a binding characteristic of an antigen-antibody complex. The functional fragment of the antibody molecule refers to a fragment having at least an antigen binding function, and may be Fab, F(ab'), F(ab')2, Fv and the like.

The monoclonal antibody of the present invention may be a monoclonal antibody including both a light-chain variable region and a heavy-chain variable region. The light-chain and heavy-chain variable regions of the monoclonal antibody of the present invention include three multivariable regions known as "complementarity-determining regions (CDRs)" and four framework regions (FRs).

The CDR mainly serves to bind to an epitope of an antigen. The CDRs of each chain are typically referred to as CDR1, CDR2, CDR3 sequentially from an N-terminus, and are also identified by a chain in which a specific CDR is located. On the other hand, the monoclonal antibody of the present invention can be produced by conjugating a framework region (FR) of a known therapeutic antibody to a complementarity-determining region (CDR). The present invention provides a base sequence of CDRs for the light-chain and heavy-chain variable regions of the monoclonal antibody.

Since the affinity of the complex is determined by the light-chain and heavy-chain variable regions, particularly, the CDRs, which are the major parts of the antibody that recognizes a specific epitope of the antigen to form an antigen-antibody complex, a gene base sequence for the variable regions of the heavy chain and the light chain of the antibody may be analyzed by cloning a monoclonal antibody gene in advance. In order to analyze the base sequence, RNA may be extracted from a fusion cell line and subjected to RT-PCR using a mouse Ig-primer set (Novagen, Calif., USA), etc.

In this specification, the term "kit" may include one or more other constituting compositions, solutions or devices suitable for the analyzing method.

For the purposes of the present invention, a monoclonal antibody produced from a hybridoma cell line of Accession Number KCLRF-BP-00389 (Accession Date: Jan. 9, 2017, Accession Institute: Korea Cell Line Research Foundation (KCLRF)) may be used. Eosinophil-derived neurotoxin (EDN) contained in a sample is bound to the monoclonal antibody in a first reaction part 120 and then reaches a second reaction part 140 while moving through a developing membrane 130 to be detected by binding with the monoclonal antibody in the second reaction part 140. Since the monoclonal antibody includes at least one marker selected from the group consisting of markers such as gold, horseradish peroxidase (HRP), alkaline phosphatase, fluorescein, and a pigment, when the color of the second reaction part is developed, the color development may be detected as asthma or allergy disease.

In addition, the kit may include all biological or chemical reagents and guidebooks required for screening antibody producing cell lines. The guidebook is a printed matter to describe a kit using method, for example, reaction conditions to be presented and the like. The guidebook may include a description on the surface of a package that includes a guidebook in the form of a brochure or leaflet, a label attached to the kit, and a kit. In addition, the guidebook may include information that is disclosed or provided through an electronic medium, such as the Internet.

In this specification, the term "asthma" refers to a disease in which symptoms such as dyspnea, coughing, and rough breathing occur repeatedly and spasmodically, and the "allergy" refers to a phenomenon in which a living body in contact with an exogenous substance exhibits a different response to the substance from a normal. The allergy is classified into I type, II type, III type, and IV type. For the purposes of the present invention, a monoclonal antibody produced from a hybridoma cell line of Accession Number KCLRF-BP-00389 (Accession Date: Jan. 9, 2017, Accession Institute: Korea Cell Line Research Foundation (KCLRF)) may be used. Eosinophil-derived neurotoxin (EDN) contained in a sample is bound to the monoclonal antibody in a first reaction part 120 and then reaches a second reaction part 140 while moving through a developing membrane 130 to bind with the monoclonal antibody in the second reaction part 140, thereby diagnosing and detecting asthma, allergy, and wheezing.

A kit for asthma diagnosis according to an exemplary embodiment of the present invention will be described with reference to FIG. 1. FIG. 1 is a schematic diagram of a strip included in a kit for asthma diagnosis according to an exemplary embodiment of the present invention.

Referring to FIG. 1, a strip 100 for asthma diagnosis according to the present exemplary embodiment includes a base part 110, a first reaction part 120 formed on the base part 110 and including a monoclonal antibody, and a developing membrane 130 formed between the first reaction part 120 and the base part 110. The developing membrane 130 is in contact with the first reaction part 120. The developing membrane 130 includes a second reaction part 140 including a monoclonal antibody and a control part 150 spaced apart from the second reaction part 140 at a predetermined interval.

In the kit for asthma diagnosis according to the present exemplary embodiment, eosinophil-derived neurotoxin (EDN) included in a sample binds with the monoclonal antibody in the first reaction part 120 and then reaches the second reaction part 140 while moving through the developing membrane 130 to be detected by binding with the monoclonal antibody in the second reaction part 140. It can be confirmed that the EDN is present in the sample by confirming the binding between the EDN-bound monoclonal antibody derived from the first reaction part and the monoclonal antibody derived from the second reaction part in the second reaction part 140, and accordingly, it can be determined that the patient where the sample is extracted suffers from asthma. The kit for asthma diagnosis according to the present exemplary embodiment may diagnose asthma or allergy disease by immunochromatography using an immune response between the antigen EDN and the monoclonal antibody. The EDN is higher in patients with asthma and allergy diseases than in normal people.

The sample may be extracted from a subject, for example, whole blood, serum, plasma, nasal lavage fluid, bronchoalveolar lavage fluid, sputum, lymph fluid or intercellular fluid. The subject, that is, an object to be inspected is not particularly limited, but may be infants or children.

The diagnostic kit according to the present exemplary embodiment may diagnose asthma more accurately and quickly by diagnosing the asthma in two steps through the monoclonal antibody derived from the first reaction part binding to the EDN and the monoclonal antibody derived from the second reaction part.

In the monoclonal antibody derived from the first reaction part, an epitope site of the EDN is attached to an idiotype of a complement determining region (CDR) of antibody. The monoclonal antibody may be produced from a hybridoma cell line of Accession Number KCLRF-BP-00389 (Accession Date: Jan. 9, 2017, Accession Institute: Korea Cell Line Research Foundation (KCLRF)). The hybridoma cell line may be produced by conventional methods known to those skilled in the art. For example, the hybridoma cell line may be produced by fusing a spleen cell of a mouse inoculated with an EDN antigen and a mouse derived myeloma cell, but is not limited thereto. Methods for obtaining monoclonal antibodies from hybridoma cell lines are by conventional methods known to those skilled in the art.

In the monoclonal antibody derived from the second reaction part, an epitope site of the EDN is attached to an idiotype of a complement determining region (CDR) of antibody. The monoclonal antibody may be expressed from a hybridoma cell line of Accession Number KCLRF-BP-00389 (Accession Date: Jan. 9, 2017, Accession Institute: Korea Cell Line Research Foundation (KCLRF)). The monoclonal antibody derived from the second reaction part may be produced by binding an enzyme to a monoclonal antibody. The enzyme may be horseradish peroxidase (HRP), alkaline phosphatase, or the like. Methods for binding the enzyme to the antibody are by conventional methods known to those skilled in the art.

When using the strip for emergency diagnosis of asthma or allergy disease using the immunochromatographic method according to the present invention, in the case of patients with asthma and allergy diseases, EDN at a high level is easily and economically tested, so that asthma or allergy disease which is not easily diagnosed in infants or children in the related art may be rapidly diagnosed at the outside or at home.

Hereinafter, the kit for asthma diagnosis according to an exemplary embodiment of the present invention will be described in more detail.

The base part 110 supports the first reaction part and the developing membrane, and may be made of a material commonly known to those skilled in the art. For example, the base part 110 may be formed of plastic, a metal material, or nitrocellulose film.

The first reaction part 120 may include a monoclonal antibody. The first reaction part 120 may include the monoclonal antibody itself, but a coloring effect may be obtained in the developing membrane by binding gold to the monoclonal antibody. The monoclonal body binding with gold may exhibit a pink color. In the method of binding gold to the monoclonal body, gold particles may be bound to a monoclonal antibody by mixing the monoclonal antibody with a gold-ion-containing compound (e.g., colloidal gold) and then reducing the gold-ion. The average particle diameter of the gold particles may be 10 nm to 100 nm. Within this range, there may be more excellent detection effects.

The first reaction part 120 may be connected to a sample injection part to receive a sample extracted from the patient. Although not illustrated in FIG. 1, a filter pad is connected to the first reaction part 120 so that the sample extracted from the patient passes through the filter pad before introduced into the first reaction part 120 to be introduced into the first reaction part 120 by removing impurities and the like, thereby more enhancing reliability of asthma diagnosis.

The first reaction part 120 is formed on a bonding pad formed of polyester fiber, glass fiber, or plant fiber, thereby stably including a first monoclonal antibody. For example, the bonding pad may be a cellulose pad.

The developing membrane 130 is in contact with the first reaction part 120 so that a combination of the EDN and the monoclonal antibody in the sample moving from the first reaction part 120 through a capillary phenomenon may move through the second reaction part 140 and the control part 150.

The second reaction part 140 includes the monoclonal antibody to bind with the EDN. The result of binding the EDN to the monoclonal antibody derived from the first reaction part and the monoclonal antibody derived from the second reaction part may be confirmed through color development. As a result of color development, the second reaction part may become pink. As described above, in the color development, the gold particles may be attached to the monoclonal antibody derived from the first reaction unit, but markers such as horseradish peroxidase (HRP), alkaline phosphatase, fluorescein, and a pigment may be used as other general methods. A color developing substrate for inducing color development is preferably used according to a marker which causes color development, and 3,3',5,5'-tetramethyl benzidine (TMB), [2,2'-azino-bis(3-ethylbenzothiazoline-6-sulfonic acid)] (ABTS), o-phenylenediamine (OPD), and the like, may be used.

The control part 150 is formed in the developing membrane 130 to determine whether the diagnostic kit operates normally and the diagnostic test has been completed.

The control part 150 informs that the sample moves to the first reaction part and the second reaction part and the test is completed, regardless of whether the sample contains EDN. A rabbit-derived anti-mouse immunoglobulin (IgG) antibody is included in the control part 150 and thus it can be seen that a non-EDN-bound monoclonal antibody included in the first reaction part reaches the control part while moving through the developing membrane to react with the anti-mouse immunoglobulin antibody, and then the test is completed. The monoclonal antibody binding with the rabbit-derived anti-mouse immunoglobulin exhibits a pink color and it is meant that when the control part exhibits the pink color, the diagnosis is completed.

The developing membrane 130 is a porous thin film and may include at least one of nylon, polyester, cellulose, polysulfone, polyvinylidene fluoride, cellulose acetate, polyurethane, glass fiber, and nitrocellulose, so that the sample is developed to the second reaction part 140 and the control part 150. It is preferable to use a phosphate buffer solution, a saline solution, Tris-HCl, water or the like as a developing reagent.

As illustrated in FIG. 1, the strip 100 may include an absorption pad 160. The absorption pad may absorb the sample passing through the control part 150 and antibody residues.

Although not illustrated in FIG. 1, the kit for asthma diagnosis according to the present exemplary embodiment may be configured such that the strip 100 is fixed, and a housing may be included on the strip 100 to prevent external contact and contamination of the first reaction part, the second reaction part, and the control part. The housing is formed of a material that does not react with any reagent, and may be formed of, for example, glass or plastic.

In addition, the diagnostic kit of the present invention may quantify EDN by a monoclonal antibody, so that asthma or allergy disease may be diagnosed superior to TEC or ECP, which has been conventionally used, and the difference in severity may be reflected.

As described above, the kit for asthma diagnosis according to an exemplary embodiment of the present invention has been described, but since the EDN is an effective antigen even in allergy disease, the EDN may be used for diagnosis of allergy disease.

Hereinafter, the configuration and operation of the present invention will be described in more detail with reference to preferred Examples of the present invention. However, this is a preferred example of the present invention and it cannot be understood that the present invention is limited thereto in any meaning.

Example 1: Preparation of Hybridoma Cell Line 50 to 100 micrograms of a native EDN antigen dissolved in a Freund's complete adjuvant was intravenously injected into female BALB/c mice (6 to 8 weeks old). 50 to 100 micrograms of an EDN antigen dissolved in PBS or an incomplete adjuvant was injected every 2 to 3 weeks. After the final injection of the EDN antigen, antibody formation was confirmed by hemorrhage in the mouse eye. Once the antibody formation was confirmed, 100 to 200 micrograms of the antibody are continuously injected for 3 to 4 days. The mice were dissected and sterilized in 70% alcohol. The spleen was removed and the spleen cells were washed, centrifuged and suspended in a serum-free medium.

The spleen cells were fused with myeloma cells obtained from a P3X63Ag8.653 mouse cell line at a ratio of 1.5:1.1. From this, a hybridoma cell line was selected. The prepared hybridoma cell line was deposited in the Korean Cell Line Research Foundation (KCLRF) on Jan. 9, 2017 to receive Accession Number KCLRF-BP-00389.

Example 2: Preparation of Monoclonal Antibody

The hybridoma cell line of Example 1 was cultured in a tissue culture flask to produce monoclonal antibodies. Specifically, $5 \times 10^6$ cells were added to 25 ml of DMEM (Gibco BRL, U.S.A.) in a 75 $cm^2$ tissue culture flask and then overgrown for 4 to 5 days in a 37 cell incubator, and then a cell culture medium was collected. The collected cell culture medium was centrifuged at 1500 rpm for 15 minutes to remove cellular components and recover only a supernatant, thereby completing production of the monoclonal antibodies. The monoclonal antibodies produced were stored at 4° C. or −20° C. until used for testing.

The gold colloid was bound to the monoclonal antibody. That is, after gold chloride was reduced with a sodium citrate solution to prepare plain gold, gold particles binding with an antibody having a size of 40 nm were prepared to have absorbance of 10±1 at a wavelength of 532 nm by adding the prepared monoclonal antibody. The antibody bound to gold particles was treated with a polyethylene glycol (PEG) solution to be stabilized. Thus, the monoclonal antibodies were prepared.

Example 3: Preparation of Monoclonal Antibody

The monoclonal antibody was prepared in the same manner except that the gold colloid was not bound.

Example 4: Preparation of Diagnostic Kit

The gold conjugate obtained by binding the gold particles prepared in Example 2 with the monoclonal antibody was mixed with 8.3 microliters/strip per strip and wetted with polyester fiber or glass fiber and dried to prepare a bonding pad including a first reaction part.

The monoclonal antibody prepared in Example 3 was diluted with PBS at a concentration of 0.75 microgram/strip per strip and coated on a nitrocellulose developing membrane at the position of a second reaction part to form the second reaction part. A rabbit anti-mouse antibody was coated on a position of a control part of the developing membrane at a concentration of 0.75 microgram/strip to form the control part.

The prepared bonding pad was superimposed on the prepared developing membrane to be cutout in size of 4.45 mm/strip, and then mounted on a plastic housing to prepare a kit for asthma or allergy disease diagnosis.

Figure 2A:
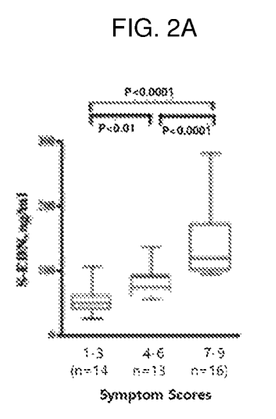
FIGS. 2A, 2B and 2C illustrate results of comparing asthma symptom scores with an EDN, an ECP, and a total eosinophil count measured by an ELISA method.
Figure 2B:
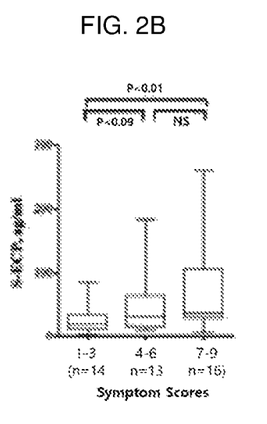
Figure 2C:
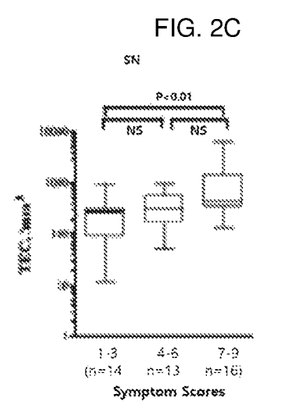

Experimental Example 1: Screening of Biomarker for Rapid Diagnosis of Asthma or Allergy Disease In order to prove the superiority of EDN used for the diagnosis of asthma or allergy in the present invention compared to a total eosinophil count (TEC) or an eosinophil cationic protein (ECP) which has been used for the diagnosis of asthma or allergy in the related art, asthma or allergy symptom scores and EDN, ECP, and the total eosinophil count measured by ELISA method were compared with each other. As a result, as illustrated in FIGS. 2A, 2B, and 2C, the EDN reflected well a difference for the severity of each asthma or allergy symptom score compared to the TEC or the ECP. Therefore, it was confirmed that the EDN may be used as a useful antigen in the diagnosis of asthma or allergy.

Figure 3:
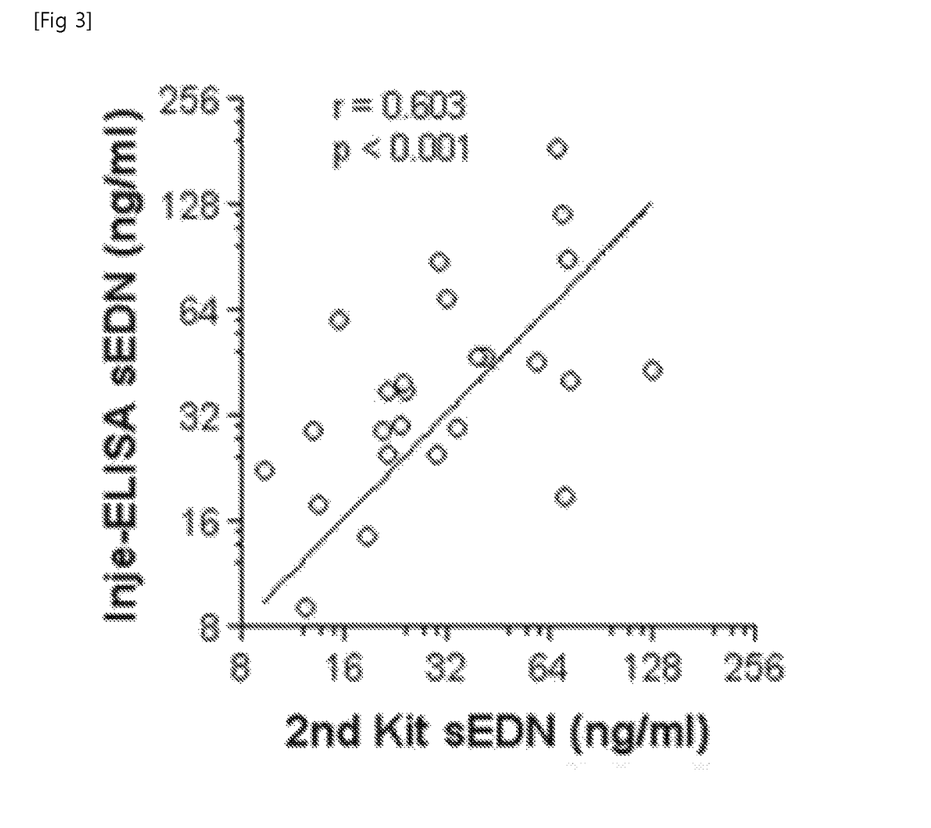
FIG. 3 illustrates a correlation between the kit for asthma diagnosis according to the present invention and diagnosis by an ELISA method.

Experimental Example 2: Comparison of Diagnostic Results with ELISA 80 serum samples with an EDN concentration of 0.62 ng/ml or more in a 5-year-old infant diagnosed with asthma or allergy and 50 normal serum samples with no asthma or allergy at the same age were obtained and tested by a diagnostic kit of the present invention and an ELISA method. As illustrated in FIG. 3, a correlation between the diagnostic kit of the present invention and the ELISA method was excellent at r=0.603 and P<0.001, so that the diagnostic kit of the present invention showed sufficient results to be used as a rapid diagnostic kit.

Experimental Example 3: Comparison of Diagnosis Results with MBL and BF Kits

Figure 4:
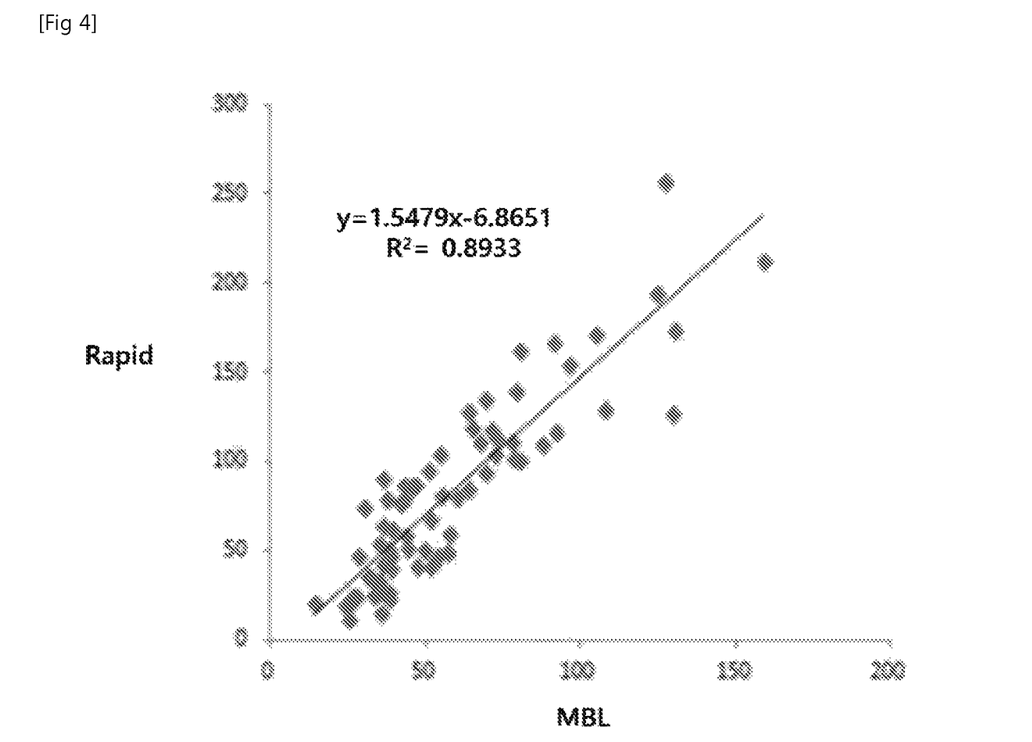
FIG. 4 illustrates a correlation (r=0.8933) between the kit for asthma diagnosis according to the present invention and diagnosis by MBL.
Figure 5:
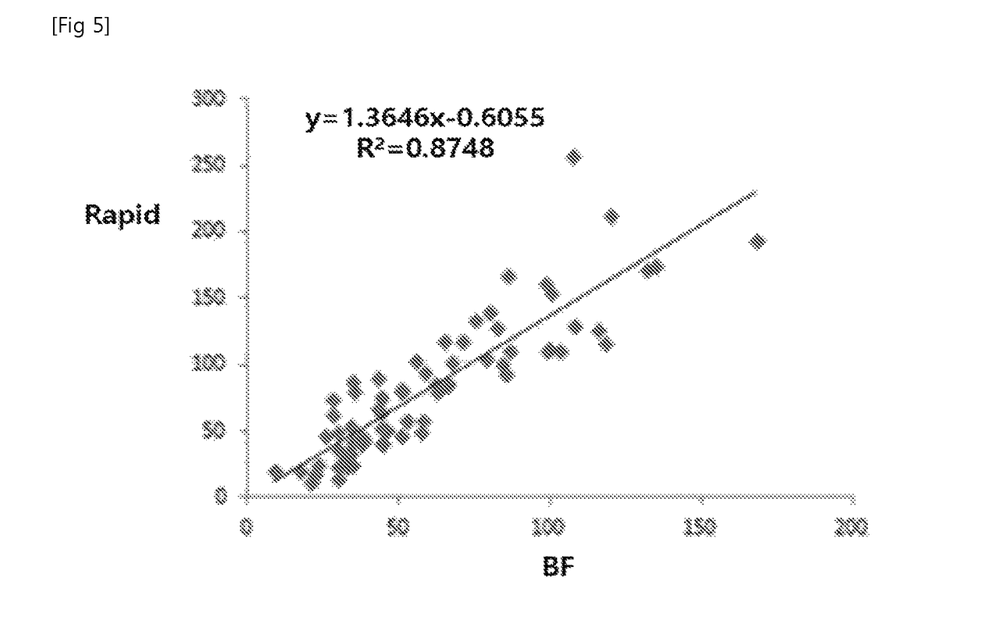
FIG. 5 illustrates a correlation (r=0.8748) between the kit for asthma diagnosis according to the present invention and diagnosis by BF.

For the same samples as in Experimental Example 2, the diagnostic kit (Rapid) of the present invention and an MBL (MEDICAL & BIOLOGICAL LABORATORIES CO., LTD) kit and a BF kit known as conventional asthma and allergy diagnostic kits were compared with each other and tested. As illustrated in FIGS. 4 and 5, a correlation between the diagnostic kit of the present invention and the test by the MBL kit and the BF kit was excellent at r=0.8933 and r=0.8748, so that the diagnostic kit of the present invention showed sufficient results to be used as a rapid diagnostic kit.

Simple modifications and changes of the present invention can be easily invented by those skilled in the art and these modifications and changes are included in the scope of the present invention.

Accession Number

Accession Institute Name: Korea Cell Line Research Foundation (KCLRF)
Accession Number: KCLRF-BP-00389
Accession Date: Jan. 9, 2017

The invention claimed is:
1. A kit for asthma diagnosis, the kit comprising a strip including:
   a base part;
   a first reaction part located on the base part and including a monoclonal antibody expressed from a hybridoma cell line (Accession Number KCLRF-BP-00389); and
   a developing membrane located between the first reaction part and the base part and including a second reaction part including the monoclonal antibody expressed from the hybridoma cell line (Accession Number KCLRF-BP-00389).
2. The kit for asthma diagnosis of claim 1, wherein the monoclonal antibody is bound with at least one marker selected from the group consisting of gold, horseradish peroxidase (HRP), alkaline phosphatase, fluorescein, and a pigment.
3. The kit for asthma diagnosis of claim 1, wherein the developing membrane further includes a control part including an anti-mouse immunoglobulin (IgG) antibody.
4. The kit for asthma diagnosis of claim 1, wherein when a color of the second reaction part is developed, the color development is diagnosed as asthma.
5. A kit for allergy diagnosis, the kit comprising a strip including:
   a base part;
   a first reaction part located on the base part and including a monoclonal antibody expressed from a hybridoma cell line (Accession Number KCLRF-BP-00389); and
   a developing membrane located between the first reaction part and the base part and including a second reaction part including the monoclonal antibody expressed from the hybridoma cell line (Accession Number KCLRF-BP-00389).
6. The kit for allergy diagnosis of claim 5, wherein the monoclonal antibody is bound with at least one marker selected from the group consisting of gold, horseradish peroxidase (HRP), alkaline phosphatase, fluorescein, and a pigment.
7. The kit for allergy diagnosis of claim 5, wherein the developing membrane further includes a control part including an anti-mouse immunoglobulin (IgG) antibody.
8. The kit for allergy diagnosis of claim 5, wherein when a color of the second reaction part is developed, the color development is diagnosed as allergy.

* * * * *